United States Patent [19]

Tocker

[11] Patent Number: 4,481,215

[45] Date of Patent: Nov. 6, 1984

[54] INSECTICIDAL COMPOSITIONS HAVING HIGH CONCENTRATION OF ACTIVE INGREDIENTS

[75] Inventor: Stanley Tocker, Wilmington, Del.

[73] Assignee: E. I. Du Pont De Nemours and Company, Wilmington, Del.

[21] Appl. No.: 483,726

[22] Filed: Apr. 18, 1983

Related U.S. Application Data

[63] Continuation-in-part of Ser. No. 387,742, Jun. 11, 1982, abandoned.

[51] Int. Cl.$^3$ .............................................. A01N 37/00
[52] U.S. Cl. ................................................... 424/298
[58] Field of Search ......................................... 424/298

[56] References Cited

U.S. PATENT DOCUMENTS

| | | | |
|---|---|---|---|
| 3,217,037 | 11/1965 | Payne, Jr. et al. | 424/320 |
| 3,530,220 | 9/1970 | Buchanan | 424/320 |
| 3,574,736 | 4/1971 | Fuchs | 260/543.1 |
| 3,576,834 | 4/1971 | Buchanan | 424/304 |
| 3,755,403 | 8/1973 | Belling | 424/298 |
| 3,767,808 | 10/1973 | Aldor et al. | 424/298 |
| 3,787,470 | 1/1974 | Buchanan | 260/453 R |
| 3,824,320 | 7/1974 | Buchanan | 424/298 |
| 4,032,654 | 6/1977 | Corty | 424/298 |
| 4,198,427 | 4/1980 | Buchanan | 424/298 |
| 4,307,115 | 12/1981 | Klopping | 424/298 |

*Primary Examiner*—Jerome D. Goldberg
*Assistant Examiner*—John M. Kilcoyne

[57] ABSTRACT

Liquid insecticidal compositions having a high concentration of active ingredients are formed from a carbamate insecticide, a reaction product of the insecticide and formaldehyde or paraformaldehyde, and 1–35% by weight, based on the weight of the composition, of water.

12 Claims, No Drawings

INSECTICIDAL COMPOSITIONS HAVING HIGH CONCENTRATION OF ACTIVE INGREDIENTS

RELATED APPLICATION

This application is a continuation-in-part of my copending application U.S. Ser. No. 387,742, filed June 11, 1982 now abandoned

BACKGROUND OF THE INVENTION

This invention relates to liquid insecticidal compositions whose active ingredients are a carbamate insecticide and a reaction product of the insecticide and formaldehyde or paraformaldehyde. The compositions contain only 1-35% by weight of water, thereby providing liquid compositions of solid insecticides having an unusually high concentration of active ingredients.

Insecticidal compositions of the carbamate insecticide methomyl and a reaction product of methomyl and formaldehyde are disclosed in U.S. Pat. No. 4,198,427 issued Apr. 15, 1980, to Buchanan. The patent further discloses that the compositions can be used in formulation with a water carrier, but only formulations having a relatively low concentration of active ingredients are discussed. Although these formulations are exceptionally effective insecticides, the low concentration of active ingredients requires high volume application. Additionally, although it is often desirable to prepackage and commercialize such compositions with water, compositions initially formulated to have greater than 35% by weight of water are often unstable at ambient temperatures in that methomyl can crystallize out of solution or, when ambient temperatures are low, the formulation can freeze. Crystallization of the carbamate can also occur upon diluting such formulations further with water, which can prevent proper distribution of the insecticide in the formulation and can clog spray nozzles during application of the formulation.

The present invention improves upon the compositions of U.S. Pat. No. 4,198,427 by providing a formulated composition having all the advantages of former compositions, such as effective insect control, and additionally being surprisingly stable at low temperatures and capable of dilution in all proportions without the occurrence of crystallization.

SUMMARY OF THE INVENTION

The present invention provides an insecticidal composition consisting essentially of:

(1) a carbamate insecticide of formula I $$R^2-O-\overset{\overset{O}{\|}}{C}-\underset{\underset{R^1}{|}}{N}H \quad \quad I$$

where $R^1$ is H or $CH_3$ and $R^2$ is selected from the group consisting of $$R^3-\underset{\underset{S-R^4}{|}}{C}=N-$$

where $R^3$ and $R^4$ are independently $C_1$-$C_3$ alkyl;

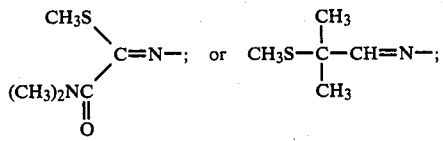

(2) a reaction product of formaldehyde or paraformaldehyde and the carbamate insecticide; and (3) 1-35% by weight, based on the weight of the composition, of water.

DETAILED DESCRIPTION OF THE INVENTION

The carbamate insecticides useful in the practice of the present invention are well known for their effectiveness and are capable of preparation by known methods. The preferred insecticides are those represented by formula I when it is as follows:

$$R^3-\underset{\underset{SR^4}{|}}{C}=N-O-\overset{\overset{O}{\|}}{C}-\underset{\underset{R^1}{|}}{N}H$$

where $R^1$ is H or $CH_3$, and $R^3$ and $R^4$ are the same or different and are $C_1$-$C_3$ alkyl, which can be branched, straight chain, or cycloalkyl. Preparation of these insecticides is described in U.S. Pat. Nos. 3,574,736; 3,576,834; and 3,787,470. Most preferred among the group of insecticides is the compound wherein $R^1$=$R^3$=$R^4$=$CH_3$; that is, the methyl ester of methyl N-(N-methylaminocarbonyloxy)ethanimidothioic acid, commonly known as methomyl.

Other carbamate insecticides useful in the practice of the present invention are:

Methyl N',N'-dimethyl-N-[(methylcarbamoyl)oxy]-1-thiooxamimidate, commonly known as oxamyl, and represented by formula I when $R^1$ is $CH_3$ and $R^2$ is

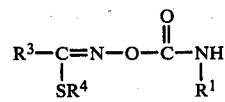

Oxamyl can be prepared as described in U.S. Pat. No. 3,530,220.

2-Methyl-2(methylthio)propionaldehyde-O-(methylcarbamoyl) oxime, commonly known as aldicarb, and represented by formula I when $R^1$ is $CH_3$ and $R^2$ is

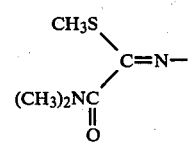

Aldicarb can be prepared as described in U.S. Pat. No. 3,217,037.

PREPARATIONS

The reaction product of the formula I insecticide and either formaldehyde or paraformaldehyde is prepared by reacting the insecticide with the paraformaldehyde in the presence of a very limited amount of water and base. When the insecticide is reacted with paraformaldehyde, those skilled in the art will recognize that the actual reaction of the insecticide is with formaldehyde, which is generated from the paraformaldehyde. Although paraformaldehyde is the preferred source of formaldehyde, as explained below, the desired reaction product is a methylol derivative of the insecticide, and therefore formaldehyde from other sources can be used as well in the reaction.

If $R_1$ in the formula I is methyl, the reaction process is represented by Equation A.

Equation A

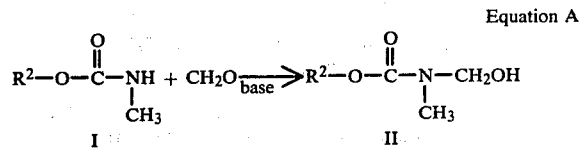

Although Equation A is represented as resulting in a simple reaction compound, represented by Formula II, it is to be understood that other constituents can also be produced, but the compounds of formula II will predominate in the reaction product. Illustrative of the other constituents that can be produced are those formed by the further reaction of formaldehyde with the initially-formed product (II). Such products are represented by Formula III.

III

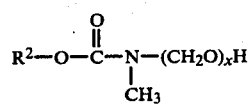

where $x=2,3,4$ (higher integers also are possible).

As used herein, the term "reaction product" includes all the compounds formed in the reaction of formaldehyde or paraformaldehyde and a compound of formula I. Excluded from the meaning of the term are the unreacted compound of formula I and any unreacted formaldehyde or formaldehyde-source compound.

When $R^1$ in formula I is hydrogen, the reaction with the formaldehyde or paraformaldehyde is represented by Equation B, and a mixture of reaction products is formed, comprised primarily of the monomethylol derivative (formula IV) with a lesser amount of the dimethylol derivative (formula V).

Equation B

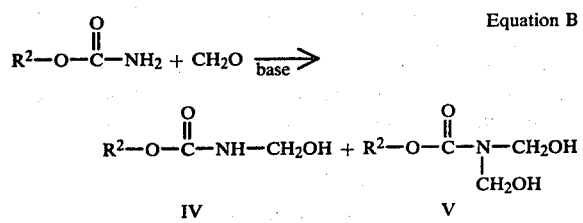

Further reaction of the formaldehyde with the hydroxyl functions of the compounds of formulae IV and V can also take place, forming additional reaction products analogous to the compounds of formula III produced by the reaction of Equation A. Nevertheless, the compounds of formula IV will predominate as the product of the reaction of Equation B.

In either of reactions A or B, a small proportion of the starting material of formula I does not react. This unreacted material, as well as some unreacted paraformaldehyde or formaldehyde, can therefore be present in the final composition.

In the reaction of insecticide of Formula I and formaldehyde or paraformaldehyde, according to either reaction A or B, the molar ratio of insecticide to formaldehyde, from whatever source, can vary from 1:0.75 to 1:2. The preferred ratio is about 1:1. It will be understood that the desired amount of pure paraformaldehyde, for example, is that amount of paraformaldehyde capable of generating the approximately equal weight like molar value of formaldehyde.

The reaction is generally carried out by contacting the insecticide and formaldehyde or paraformaldehyde, together with a base, in the presence of water. In this basic medium, paraformaldehyde generates the ultimate formaldehyde reactant. Surprisingly, the amount of water used to dissolve this combination of reactants can be lower than would be needed to dissolve the unreacted carbamate individually. Generally, from 1–35% by weight of water, based on the total weights of the water, formaldehyde or paraformaldehyde, and insecticide, is used. Preferably 5–20% by weight of water, and most preferably about 10–15% by weight of water, is used. Bases suitable for use in the reaction are bicarbonates, carbonates, hydroxides of alkali metals and alkaline earths, anion exchange resins, and organic bases such as tertiary alkyl amines, pyridine, and dimethylanilines. Preferred bases are the alkali metal hydroxides, particularly sodium hydroxide. The base is usually present at a concentration of 0.01–1% by weight, based on total reaction mixture weight, although the preferred concentration is such as will bring the reaction mixture to a pH of about 9–10.

The reaction process is carried out at a temperature of from 0°–100° C., preferably 35°–85° C., for about 20 minutes to 4 hours, depending on the temperature. The reaction may be run at atmospheric pressure or in a closed system, under autogenous pressure. Those skilled in the art will recognize that the reaction time will depend upon factors such as temperature, pressure, speed of agitation, concentration of the base, amount of water, etc. A preferred mode of operation is to contact the reactants at about 40° C. for 30 minutes in water (about 13% by weight, based on total mixture weight) using a sodium hydroxide catalyst to bring the reaction mixture to a pH of 9–10.

When the reaction has progressed to a sufficient level of formation of the methylol derivative of the insecticide, which can be determined for example by NMR, it is much preferred to neutralize the base or to make the reaction mixture slightly acidic for purposes of storage stability. Most preferably, the final mixture will be acidic, with a pH of about 5.0–6.8. Organic carboxylic acids, such as acetic acid, or mineral acids, such as phosphoric acid, are preferred for this use.

The choice of basic catalyst and acidification agent can affect the properties of the product upon application. The methylol derivative of Formula II is a latent form of the insecticide and reverts to the insecticide itself in vivo, a change that is accelerated by alkaline conditions. In mixtures using a non-volatile base, such as sodium hydroxide, and a volatile acid, such as acetic acid, the methylol derivative reverts to the insecticide relatively rapidly, under conditions where evaporation takes place, because the mixture will tend to become alkaline upon application. Such mixtures will dry out more quickly on foliage than will mixtures in which the reversion is slower (those using volatile bases and non-volatile acids) and will exhibit greater initial, as opposed to residual, activity.

At the completion of the reaction, the composition has a preferred weight ratio of reaction product to unreacted carbamate insecticide of from about 1.5:1 to about 20:1, more preferably up to about 3:1. A most preferred weight ratio is from about 2:1 to about 3:1. If the reaction mixture contains insufficient unreacted carbamate insecticide to attain this range, some fresh insecticide can be added to the composition. It is to be understood that the ratio of unreacted insecticide to reaction product will depend on the amount of water used because it is preferred that the amount of unreacted insecticide not exceed about 35% by weight of the total mixture weight.

Although it is preferred to perform the reaction with only one particular insecticide at a time, it is to be understood that it is quite possible, and often useful, to contact the formaldehyde or paraformaldehyde with a mixture of insecticides of formula I. In such a case, the final composition will be a mixture of the starting insecticides and the various reaction products of the insecticides with the formaldehyde or paraformaldehyde. In general, therefore, the reaction product will be comprised in substantial amount of a compound, or mixture of compounds, of the formula

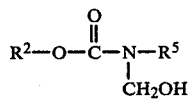

where $R^2$ is as defined previously and $R^5$ is hydrogen, methyl, or $CH_2OH$.

The final composition of this invention also contains about 1–35% by weight of water, based on the total composition weight. As mentioned, the presence of similar amounts of water is highly preferable during the formation of the methylol derivatives of the insecticide, but additional water can be added to the post-reaction mixture to bring the total water content of the resultant composition to a higher level within the above-stated range.

The outstanding properties of the final composition of this invention are due in large part to the unique combination of unreacted carbamate and the methylol carbamates of formulas II, IV, and V in the small amount of water. Surprisingly, organic solvents such as methanol, acetone, or cyclohexanone, that are generally better solvents for carbamates alone than is water, allow crystallization to occur in these compositions at low temperatures. The use of small amounts of water instead of such other solvents eliminates this problem in these compositions. Apparently, the carbamate and its methylol derivative, along with the small amounts of water used herein, act synergistically to form a stable eutectic system that has a lower freezing point than does any of the components individually.

For example, a system containing a 2:1 weight ratio mixture of N-methylolmethomyl to methomyl with 13% by total weight of water can be stored for two months at a temperature of −10° C. without the occurrence of crystallization or freezing. With a total water content of 20–35%, the composition can freeze, but can be thawed out at room temperature to a fluid without the occurrence of any crystallization. At total water concentrations of over about 45% by weight, both freezing and crystallization can take place, and furthermore, undesirable hydrolysis of the N-methylolcarbamate can also occur.

USE

The compositions of this invention are useful for the control of agriculturally destructive insects. For purposes of the present discussion, the compositions include (a) a carbamate insecticide of formula I, (b) the reaction product of formaldehyde or paraformaldehyde and the carbamate insecticide, and (c) 1–35% by weight, based on the combined weights of (a)–(c), of water. The composition can also contain some unreacted formaldehyde or paraformaldehyde. Although it is not necessary to remove the unreacted formaldehyde prior to use of the composition, it is desirable to do so. This can be done by purging with air or with an inert gas, or by adding urea to form methylolurea derivatives. Alternatively, other agents can be added that are known to react with formaldehyde to form compounds that do not adversely affect insecticidal compositions.

The compositions readily control pestiferous insects belonging to such orders as Lepidoptera, Coleoptera, Homoptera and Diptera. More specifically, insects controlled by the compounds of this invention include but are not limited to: cotton bollworm (*Heliothis zea*), tobacco budworm (*Heliothis virescens*), southern armyworm (*Spodoptera eridania*), beet armyworm (*Spodoptera exigua*), soybean looper (*Pseudoplusia includens*), Mexican bean beetle (*Epilachna varivestis*), green peach aphid (*Myzus persicae*) and the house fly (*Musca domestica*).

The insects are controlled by applying the composition to the locus of infestation, to the area to be protected, or to the pests themselves. For the control of insects in agricultural crops, the composition is generally applied to the foliage or other plant parts which are infested or which are to be protected. Effective amounts to be applied depend upon the species to be controlled, its life stage, its size and location, the amount of rainfall, the time of year, moisture, temperature, type of application, and other variables. In general, 0.01 to 5.0 kg/ha may be required for insect control in agriculture with rates of up to 2.0 kg/ha usually being sufficient. It is understood that the rates disclosed are governed in part by the concentration of the active compounds present in the composition. Higher application rates than those stated can also be used.

The compositions of the present invention possess significant advantages over similar compositions of the prior art. As mentioned, the compositions are more stable at low temperatures, resisting the undesirable tendency of the carbamate insecticide to crystallize out of solution. The composition can be applied as is or can be diluted in water or other diluent in all proportions.

An additional advantage of the compositions of the present invention is the versatile performance achievable by choice of basic catalyst and acidic stabilizer. Compositions employing volatile basic catalysts, such as triethylamine, and non-volatile acid-stabilizer, such as phosphoric acid, tend to leave a lacquer-like deposit on foliage and provide relatively long residual activity. It is surprising that even when these compositions are subsequently diluted, this slow drying property is retained over conventional liquid carbamate compositions. Conventional liquid formulations of solid insecticides can rapidly dry out after spray application leaving a crystalline residue of insecticide that is relatively easily blown off some foliage.

Alternatively, compositions employing a non-volatile basic catalyst, such as sodium hydroxide, and a volatile acid-stabilizer, such as acetic acid tend to dry out on foliage somewhat more quickly. These compositions, with somewhat less residual activity, are particularly useful in those applications where relatively high initial activity is preferred, such as where insects are to be contacted directly during application.

Carbamate insecticides, which are normally solids, are often formulated into a liquid state, to make them easier to use and apply, by dilution in inert organic solvents. The active ingredient content of these formulations is generally below 30% by weight, with the large proportions of organic solvent raising the cost and presenting other hazards. In the present invention, solid carbamate insecticides are formulated into a liquid state without the need for any organic solvent and are present in this formulation at a concentration of at least 65% by weight. The highly storage-stable compositions of the present invention can be applied as is, or can be diluted in water or other diluents in all proportions just before final application.

The present invention provides additional advantages that stem from its slow-drying properties and high concentration of active ingredients. For example, low volume applications with conventional spray equipment can be made with fewer passes than are normally used for other liquid carbamate compositions, which usually contain over 65% inert solvent to maintain the insecticide in the liquid state. This is particularly advantageous for spray applications made by airplane because of the number of landings necessary to refill spray tanks can be reduced. Also, the compositions' reduced tendency to dry out during spraying minimizes the possibility that a fine particulate mist, which can drift to undesired areas, will be formed. When used in controlled droplet size applicators, which are becoming increasingly popular with agricultural products, the present compositions permit precise application, minimizing overspray to provide safer, more efficient use.

The compositions of this invention can be further formulated in a known manner with other components such as surfactants, diluents, dyes, stickers, additives to reduce foam, corrosion or wash-off, or preservatives to control microbiological growth. The compositions of this invention can also be added to inert adsorbents, such as clay powder or diatomaceous earth granules, to give non-dusting insecticidal powders or granules with unusually high concentration of active ingredients.

The compositions of this invention can be mixed with fungicides, bactericides, acaricides, nematicides, insecticides, or other biologically active compounds in order to achieve desired results with a minimum expenditure of time, effort, and material. Amounts of these biologically active materials added for each part by weight of the composition of this invention may vary from 0.05 to 25 parts by weight. Suitable agents of this type are well-known to those skilled in the art. Some are listed below:

Fungicides:

methyl 2-benzimidazolecarbamate (carbendazim)
tetramethyl thiuram disulfide (thiuram)
n-dodecylguanidine acetate (dodine)
manangese ethylenebisdithiocarbamate (maneb)
1,4-dichloro-2,5-dimethoxybenzene (chloroneb)
methyl 1-(butylcarbamoyl)-2-benzimidazolecarbamate (benomyl)
N-trichloromethylthiotetrahydrophthalimide (captan)
N-trichloromethylthiophthalimide (folpet)
1-(4-chlorophenoxy)-3,3-dimethyl-1-(1H-1,2,4-triazol-1-yl)-2-butanone (triadimefon)
1-(4-phenylphenoxy)-3,3-dimethyl-1-(1H-1,2,4-triazol-1-yl)-2-butanol (bitertanol)
1-[2-(2,4-dichlorophenyl)-4-propyl-1,3-dioxolan-2-yl-methyl]-1H-1,2,4-triazole (propaconazole)
1-[2-(2,4-dichlorophenyl)-4-ethyl-1,3-dioxolan-2-yl-methyl]-1H-1,2,4-triazole (etaconazole)

Bactericides:

tribasic copper sulfate
streptomycin sulfate

Acaricides:

senecioic acid, ester with 2-sec-butyl-4,6-dinitrophenol (binapacryl)
6-methyl-1,3-dithiolo[2,3-B]quinonolin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyl tinhydroxide (cyhexatin)
hexakis(2-methyl-2-phenylpropyl)distannoxane (fenbutin oxide)
Fenpropathrin Nematicides:

S-methyl 1-(dimethylcarbamoyl)-N-(ethylcarbamoyloxy)thioformididate
S-methyl 1-carbamoyl-N-(methylcarbamoyloxy)thioformimidate
N-isopropylphosphoramidic acid, O-ethyl-O'-[4-(methylthio)-m-toly]diester (fenamiphos)

Insecticides:

methylcarbamic acid, ester with 2,3-dihydro-2,2-dimethyl-7-benzofuranol (carbofuran)
O-[2,4,5-trichloro-α-(chloromethyl)benzyl phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
N'-(4-chloro-o-tolyl)-N,N-dimethylformamidine (chlordimeform)
O,O-diethyl-O-(2-isopropyl-4-methyl-6-pyrimidylphosphorothioate
O,S-dimethyl acetylphosphoramidothioate (acephate)
O,S-dimethyl phosphoramidothioate (methamidophos)
O-ethyl O-(4-nitrophenyl)phenylphosphonothioate (EPN)
O,O-diethyl O-p-nitrophenylphosphorothioate (parathion)
3-(phenoxyphenyl)methyl(+)-cis,trans-3-(2,2-dichloroethenyl)-2,2-dimethylcyclopropane-carboxylate (permethrin)
(S)-α-cyano-m-phenoxybenzyl(1R,3R)-3-(2,2-dibromovinyl)-2,2-dimethylcyclopropane-carboxylate (deltamethrin)
cyano(3-phenoxyphenyl)methyl 4-chloro-α-(1-methylethyl)benzeneacetate (fenvalerate)
α-cyano-3-phenoxybenzyl 2,2-dimethyl-3-(2,2-dichlorovinyl)cyclopropane-carboxylate (cypermethrin)
1-(4-chlorophenyl)-3-(2,6-difluorobenzoyl)urea (diflubenzuron)

dimethyl N,N'-[thiobis[(N-methylimino)-carbonyloxy]-]ethanimidothioate (thiodicarb)

O,O-diethyl O-(3,5,6-trichloro-2-pyridyl) phosphorothioate (chlorpyrifos)

N-(2-chloro-4-trifluoromethylphenyl)-DL-valine (+)-cyano(3-phenoxyphenyl)methyl ester (fluvalinate)

(S)-α-cyano-3-phenoxybenzyl (1R,3R)-3-(1,2,2,2-tetrabromoethyl)-2,2-dimethylcyclopropanecarboxylate (tralomethrin)

O,O-diethyl O-(5-phenyl-3-isoxazolyl)phosphorothioate (isoxathion)

O,O-diethyl O-(1-phenyl-1H-1,2,4-triazol-3-yl)phosphorothioate (triazophos)

EXAMPLES

The following examples illustrate various aspects of the present invention.

EXAMPLE 1

To an aqueous solution of 32.88 g of 50% formaldehyde at 70° C. in an agitated 3-neck flask was added about 0.1 g 50% NaOH to adjust the pH to 9.0–10.0. Subsequently, 4.3 g water, followed by 100 g technical methomyl were added, the reaction temperature then being held at 45° C. for 30 minutes. The pH was adjusted to 6.7 with acetic acid, and 1.7 g pearled urea was added. Liquid chromatograph (high performance) analysis of the clear, solid free, amber solution that resulted showed 24.5% methomyl, 57.8% N-methylolmethomyl, and 0.57% unreacted formaldehyde. The overall methomyl content in the system (in the form of free methomyl and the methomyl derivative) was 73%.

EXAMPLE 2

A mixture of 1600 g technical methomyl, 296 g paraformaldehyde (Fisher Scientific Company), and 200 g water, containing 1.64 g 50% aqueous sodium hydroxide, was heated at 60° C. for 25 minutes to liquefy the reaction mass. The reaction mixture was then allowed to cool to 25° C. and the pH was adjusted from 9.2 to 6.6 with 2.3 g of glacial acetic acid. A solution of 28 g urea (Fisher Scientific Company) in 88 g of water was added to remove unreacted formaldehyde. Nuclear magnetic resonance analysis using deuterated chloroform as solvent showed a doublet at 2.8–2.9 ppm characteristic of the —NHCH$_3$ group of methomyl, a singlet of 3.0 ppm, corresponding to th —NCH$_3$ group of N-methylolmethomyl, and a peak at 4.8 ppm, corresponding to the —CH$_2$OH group of N-methylolmethomyl. The weight ratio of N-methylolmethomyl to methomyl was 2.4:1. The overall methomyl content (in the form of free methomyl and the methylol derivative) totaled 72%.

The product formed above was sprayed undiluted through a controlled-droplet spinning-disc sprayer, to give a uniform spray pattern, onto water-sensitive paper. The spray characteristics were compared with those of ordinary tap water, which had been sprayed in the same manner. The droplets produced by the insecticidal concentrate of this example were below 100 microns in diameter; those produced by the tap water were about 100-150 microns in diameter.

EXAMPLE 3

Example 1 was repeated except that phosphoric acid was substituted for acetic acid. This repeated example is referred to as Example 1(a). The products of Examples 1(a) and 2 were spread out on a glass plate and left in a laboratory hood overnight at 24° C. The product of Example 2 showed evidence of crystallization whereas the product of Example 1(a), in which the non-volatile phosphoric acid had been used, remained liquid. After 4 days, the product of Example 2 had almost totally reverted to methomyl whereas the product of Example 1(a) was still liquid and contained N-methylolmethomyl (by thin layer chromatography analysis on silica, using ethyl acetate as eluent). Neither product crystallized after storage for over one month in closed glass bottles at −10° C., and both were dilutable in all proportions with water without the occurrence of crystallization.

EXAMPLE 4

A mixture of 32 g methomyl, 5.9 g paraformaldehyde, 2.0 g of water and 0.1 g triethylamine was heated at 60° C. for 10 minutes, followed by acidification with phosphoric acid. The overall methomyl content was about 80% and the weight ratio of N-methylolmethomyl to methomyl was about 1.6 to 1. The mixture did not crystallize after prolonged storage at −10° C. and was dilutable in all proportions with water without crystallization.

EXAMPLE 5

A mixture of 40 g technical oxamyl (prepared by partially stripping Vydate®L followed by crystallization), 5.4 g paraformaldehyde and 10.8 g water was treated with 0.08 g 50% aqueous sodium hydroxide, and the mixture was heated at 45° C. for 1.0 hour. The pH was then adjusted to 6.7 with acetic acid, and 0.56 g urea was added to remove excess formaldehyde. NMR analysis showed N-methyloloxamyl and oxamyl in a weight ratio of approximately 2:1. The overall oxamyl content (in the form of free oxamyl and methylol derivative) was 70%. The formulation did not crystallize at −10° C. after two weeks. It was dilutable in all proportions with water.

EXAMPLE 6

The product of Example 1 was dissolved in commercial preparations of permethrin (Ambush®, which is 26% active ingredient) at weight ratios that range from 2:1 to 1:2 of active ingredients. These mixtures are stable and sprayable with or without dilution by water.

EXAMPLE 7

The composition of Example 2, in undiluted form, and a solution of methomyl were compared for both initial and residual activity. Each was sprayed onto red kidney bean plants (averaging seven inches in height) using a Micromax controlled droplet sprayer at a 30° angle setting and at a rate of 60 ft./min. The sprayed plants were maintained at 27° C., 50% relative humidity, and were exposed to 12 hours of artificial sunlight per day. From plants sprayed with each of the two insecticides, leaves were excised at intervals of one and five days after spray and then placed into separate petri dishes. Third-instar larvae of fall armyworm were placed into each petri dish, and evaluation of mortality made 48 hours after placement of the larvae in each case. The results, tabulated below, indicate that the composition of Example 2 has residual activity superior to that of methomyl itself.

| Treatment | Application Rate (pounds of active ingredient per acre) | Percent Mortality (48 hour evaluation) | |
|---|---|---|---|
| | | 1 Day | 5 Days |
| Untreated Control | — | 10 | 0 |
| Methomyl Solution | 0.02 | 95 | 45 |
| | 0.08 | 100 | 75 |
| Example 2 Composition | 0.02 | 90 | 70 |
| | 0.08 | 100 | 100 |

EXAMPLE 8

In field tests on soybeans, designed to show control of velvetbean caterpillar (*Anticasia gemmatalis*), the composition of Example 3 was tested against methomyl alone. Each of the test substances was diluted to 0.26% by weight active ingredient, and sprayed to run-off on the soybean plants. No phytotoxicity was observed, and after 11 days plants sprayed with either substance were totally free of insects.

EXAMPLE 9

In field tests on apple trees infested with aphids, the composition of Example 3 was tested against methomyl alone. Each of the test substances was diluted to 0.0078% by weight active ingredient, and sprayed to run-off on the apple trees. Test results, summarized below, were compiled by counting the number of aphids per shoot terminal at periodic intervals.

| | 7 days After Spray | 14 days After Spray |
|---|---|---|
| Untreated Control | 150 | 49 |
| Methomyl alone | 18 | 11 |
| Example 3 composition | 2 | 5 |

EXAMPLE 10

The compositions of Examples 2 and 3 were tested against the use of methomyl alone against Heliothis on cotton. The tested substances were sprayed to run-off on the plants at a rate of 225 grams of methomyl (in free form or as the methylol derivative) per hectare. The test results, summarized below, indicate that the product of Example 3, which contains a non-volatile acid as stabilizer, provides more residual activity than is provided by the product of Example 2, which contains a volatile acid stabilizer. Both products show better residual activity than methomyl.

| Composition | Percent control, 1 Week after application |
|---|---|
| Methomyl (control) | 50 |
| Example 2 | 90 |
| Example 3 | 96 |

EXAMPLE 11

The product of Example 3 (1.0 g) was hand-stirred into 4.0 grams of montmorillonite clay. The resulting mixture was a free-flowing, dustless powder that contained 16% by weight total methomyl in the form of both free methomyl and the N-methylol derivative.

Free-flowing, dustless granules containing 32% by weight total methomyl were prepared by mixing, in a similar manner, 6.0 grams of diatomaceous earth with 4.0 grams of the product of Example 3.

What is claimed is:

1. An insecticidal composition consisting essentially of
   (1) methomyl;
   (2) a reaction product of formaldehyde or paraformaldehyde and methomyl, wherein the weight ratio of reaction product to unreacted methomyl is from about 1.5:1 to about 20:1; and
   (3) 5-35% by weight, based on the weight of the composition, of water.

2. The composition of claim 1 wherein the reaction product is a compound of the formula

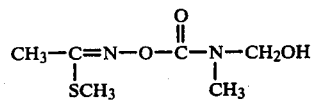

3. The composition of claim 1 wherein there is 5-20% by weight, based on the weight of the composition, of water.

4. The composition of claim 1 wherein there is 10-15% by weight, based on the weight of the composition, of water.

5. The composition of claims 1, 3, or 4 wherein the weight ratio of reaction product to unreacted methomyl is from about 2:1 to about 20:1.

6. The composition of claims 1, 3, or 4 wherein the weight ratio of reaction product to unreacted methomyl is from about 2:1 to about 3:1.

7. The composition of claim 6 wherein the composition is acidic.

8. A method for control of insects comprising applying to a locus to be protected as insecticidally effective amount of a composition of claim 1.

9. A method for control of insects comprising applying to a locus to be protected an insecticidally effective amount of a composition of claim 5.

10. A method for control of insects comprising applying to a locus to be protected an insecticidally effective amount of a composition of claim 4.

11. A method for control of insects comprising applying to a locus to be protected an insecticidally effective amount of a composition of claim 6.

12. A method for control of insects comprising applying to a locus to be protected an insecticidally effective amount of a composition of claim 7.

* * * * *